(12) United States Patent
Frantz et al.

(10) Patent No.: US 8,394,361 B1
(45) Date of Patent: Mar. 12, 2013

(54) STABLE SURFACTANT COMPOSITIONS FOR SUSPENDING COMPONENTS

(75) Inventors: Seren Frantz, Bensalem, PA (US); Phillip L. Cotrell, New Egypt, NJ (US); Stewart A. Warburton, West Windsor, NJ (US)

(73) Assignee: Rhodia Operations, Aubervilliers (FR)

( * ) Notice: Subject to any disclaimer, the term of this patent is extended or adjusted under 35 U.S.C. 154(b) by 191 days.

(21) Appl. No.: 12/965,389

(22) Filed: Dec. 10, 2010

Related U.S. Application Data

(62) Division of application No. 10/324,371, filed on Dec. 20, 2002, now Pat. No. 8,029,772.

(60) Provisional application No. 60/369,216, filed on Apr. 1, 2002.

(51) Int. Cl.
*A61K 8/00* (2006.01)

(52) U.S. Cl. ............... 424/70.21; 510/424; 510/426; 424/70.1; 424/70.22

(58) Field of Classification Search .................. None
See application file for complete search history.

(56) References Cited

U.S. PATENT DOCUMENTS

| | | |
|---|---|---|
| 3,723,325 A | 3/1973 | Parran, Jr. |
| 3,956,158 A | 5/1976 | Donaldson |
| 4,001,394 A | 1/1977 | Fogel et al. |
| 4,069,347 A | 1/1978 | McCarthy et al. |
| 4,243,549 A | 1/1981 | Messenger et al. |
| 4,395,373 A | 7/1983 | Login |
| 4,434,062 A | 2/1984 | Oswald et al. |
| 4,515,704 A | 5/1985 | Akred et al. |
| 4,536,519 A | 8/1985 | Suzuki et al. |
| 4,565,647 A | 1/1986 | Llenado |
| 4,618,446 A | 10/1986 | Haslop et al. |
| 4,659,497 A | 4/1987 | Akred et al. |
| 4,753,793 A | 6/1988 | Walton |
| 4,871,467 A | 10/1989 | Akred et al. |
| 4,933,176 A | 6/1990 | Van Reeth |
| 4,964,874 A | 10/1990 | Saphakkul |
| 4,997,641 A | 3/1991 | Hartnett et al. |
| 5,009,814 A | 4/1991 | Kelkenberg et al. |
| 5,114,706 A | 5/1992 | Duvel |
| 5,147,576 A | 9/1992 | Montague et al. |
| 5,196,187 A | 3/1993 | Nicoll et al. |
| 5,244,664 A | 9/1993 | Godtfredsen |
| 5,262,079 A | 11/1993 | Kacher et al. |
| 5,292,504 A | 3/1994 | Cardin et al. |
| 5,348,736 A | 9/1994 | Patel et al. |
| 5,358,667 A | 10/1994 | Bergmann |
| 5,364,551 A | 11/1994 | Lentsch et al. |
| 5,389,279 A | 2/1995 | Au et al. |
| 5,393,466 A | 2/1995 | Ilardi et al. |
| 5,397,493 A | 3/1995 | Potocki |
| 5,417,879 A | 5/1995 | Hall et al. |
| 5,478,490 A | 12/1995 | Russo et al. |
| 5,520,839 A | 5/1996 | Hall et al. |
| 5,556,628 A | 9/1996 | Derian et al. |
| 5,602,092 A | 2/1997 | Repinec et al. |
| 5,612,307 A | 3/1997 | Chambers et al. |
| 5,627,148 A | 5/1997 | Dubief et al. |
| 5,650,384 A | 7/1997 | Gordon et al. |
| 5,661,189 A | 8/1997 | Grieveson et al. |
| 5,683,683 A | 11/1997 | Scafidi |
| 5,716,920 A | 2/1998 | Glen et al. |
| 5,776,883 A | 7/1998 | Vasudevan |
| 5,783,533 A | 7/1998 | Kensicher et al. |
| 5,786,310 A | 7/1998 | Dubief et al. |
| 5,792,472 A | 8/1998 | Roux et al. |
| 5,807,810 A | 9/1998 | Blezrd et al. |
| 5,840,789 A | 11/1998 | Verstrat et al. |
| 5,851,978 A | 12/1998 | Shana'a |
| 5,858,938 A | 1/1999 | Glenn, Jr. et al. |
| 5,908,697 A | 6/1999 | Roux et al. |
| 5,910,302 A | 6/1999 | Herter et al. |
| 5,916,575 A | 6/1999 | Mc Atee et al. |
| 5,925,364 A | 7/1999 | Ribler et al. |
| 5,929,019 A | 7/1999 | Puvvada et al. |
| 5,932,528 A | 8/1999 | Glenn, Jr. et al. |
| 5,935,915 A | 8/1999 | Gordon et al. |
| 5,952,285 A | 9/1999 | Hawkins |
| 5,952,286 A | 9/1999 | Puvvada et al. |
| 5,962,395 A | 10/1999 | Puvvada et al. |
| 5,964,692 A | 10/1999 | Blezard et al. |
| 5,965,500 A | 10/1999 | Puvvada |
| 5,997,854 A | 12/1999 | Von Mallek |
| 6,066,328 A | 5/2000 | Ribier et al. |
| 6,066,607 A | 5/2000 | Gordon |
| 6,066,608 A | 5/2000 | Glenn, Jr. |
| 6,074,633 A | 6/2000 | Dubief et al. |
| 6,077,816 A | 6/2000 | Puvvada et al. |
| 6,080,707 A | 6/2000 | Glenn, Jr. et al. |

(Continued)

FOREIGN PATENT DOCUMENTS

| | | |
|---|---|---|
| DE | 4 330 597 | 3/1995 |
| EP | 0 151 884 | 8/1985 |

(Continued)

OTHER PUBLICATIONS

Japanese Patent Office, Notice of Reason for Rejection, mailed May 10, 2011, regarding Japanese Application No. 2008/014137, pp. 1-9 (English Language Translation).

EspaceNet Patent Search Website Family for U.S. Patent No. 4,997,641.

EspaceNet Patent Search Website Family for EP Patent Doc. No. 3 312 234.

EspaceNet Patent Search Website Family for EP Patent Doc. No. EP 0 471 606.

(Continued)

*Primary Examiner* — Hasan Ahmed

(74) *Attorney, Agent, or Firm* — Hunton and Williams, LLP

(57) ABSTRACT

A free-flowing surfactant composition comprising at least one anionic surface-active agent, an alkanolamide, an electrolyte, and water is described. In particular, the composition is a surfactant composition that has free-flowing non-Newtonian shear thinning properties and the ability to suspend components and is stable under at least one freeze/thaw cycle.

12 Claims, No Drawings

U.S. PATENT DOCUMENTS

| | | | |
|---|---|---|---|
| 6,080,708 | A | 6/2000 | Glenn, Jr. et al. |
| 6,150,312 | A | 11/2000 | Puvvada et al. |
| 6,174,846 | B1 | 1/2001 | Villa |
| 6,177,390 | B1 | 1/2001 | Guskey et al. |
| 6,177,396 | B1 | 1/2001 | Clapperton et al. |
| 6,194,364 | B1 | 2/2001 | Glenn, Jr. |
| 6,200,937 | B1 | 3/2001 | Brennan et al. |
| 6,235,275 | B1 | 5/2001 | Chen et al. |
| 6,258,859 | B1 | 7/2001 | Dahayanake et al. |
| 6,280,758 | B1 | 8/2001 | Warren et al. |
| 6,287,583 | B1 | 9/2001 | Warren et al. |
| 6,294,179 | B1 | 9/2001 | Lee et al. |
| 6,325,995 | B1 | 12/2001 | El-Nokaly et al. |
| 6,358,497 | B2 | 3/2002 | Parry et al. |
| 6,376,438 | B1 | 4/2002 | Rosenberger et al. |
| 6,395,690 | B1 | 5/2002 | Tsaur |
| 6,416,768 | B1 | 7/2002 | Ravaux et al. |
| 6,426,326 | B1 | 7/2002 | Mitra et al. |
| 6,429,177 | B1 | 8/2002 | Williams et al. |
| 6,432,420 | B2 | 8/2002 | Ellis et al. |
| 6,444,629 | B1 | 9/2002 | Elliott et al. |
| 6,479,446 | B1 | 11/2002 | Sherry et al. |
| 6,482,866 | B1 | 11/2002 | Dahayanake et al. |
| 6,506,391 | B1 | 1/2003 | Biatry |
| 6,506,710 | B1 | 1/2003 | Hoey et al. |
| 6,534,456 | B2 | 3/2003 | Hayward et al. |
| 6,534,457 | B2 | 3/2003 | Mitra |
| 6,660,699 | B2 | 12/2003 | Finucane et al. |
| 6,673,755 | B2 | 1/2004 | Wei et al. |
| 6,677,294 | B2 | 1/2004 | Shaw et al. |
| 6,682,723 | B2 | 1/2004 | Parry et al. |
| 6,706,144 | B1 | 3/2004 | Furman et al. |
| 6,726,902 | B1 | 4/2004 | Muller et al. |
| 6,770,612 | B1 | 8/2004 | Hatchman |
| 2002/0009425 | A1 | 1/2002 | Cannell et al. |
| 2002/0012647 | A1 | 1/2002 | Cannell et al. |
| 2002/0028755 | A1 | 3/2002 | Van Dijk et al. |
| 2002/0034489 | A1 | 3/2002 | Wiegland et al. |
| 2002/0071819 | A1 | 6/2002 | Giles et al. |
| 2002/0119113 | A1 | 8/2002 | Ellis et al. |
| 2002/0187904 | A1 | 12/2002 | Perron et al. |
| 2003/0083210 | A1 | 5/2003 | Goldberg et al. |
| 2003/0171231 | A1 | 9/2003 | Shana'a et al. |
| 2003/0180246 | A1 | 9/2003 | Frantz et al. |
| 2003/0190302 | A1 | 10/2003 | Frantz et al. |
| 2004/0057920 | A1 | 3/2004 | Focht et al. |
| 2004/0092415 | A1 | 5/2004 | Focht et al. |
| 2004/0143269 | A1 | 7/2004 | Pude et al. |
| 2004/0219991 | A1 | 11/2004 | Wei et al. |
| 2004/0223991 | A1 | 11/2004 | Wei et al. |
| 2004/0234565 | A1 | 11/2004 | Stella et al. |
| 2004/0235693 | A1 | 11/2004 | Wei et al. |
| 2004/0235702 | A1 | 11/2004 | Hawkins |
| 2004/0248748 | A1 | 12/2004 | Wei et al. |
| 2005/0020468 | A1 | 1/2005 | Frantz et al. |
| 2005/0025731 | A1 | 2/2005 | Knopf et al. |
| 2005/0100570 | A1 | 5/2005 | Wei et al. |
| 2005/0124526 | A1 | 6/2005 | D'Angelo et al. |
| 2005/0143268 | A1 | 6/2005 | Midha et al. |
| 2005/0192187 | A1 | 9/2005 | Wagner et al. |
| 2005/0192188 | A1 | 9/2005 | Wagner et al. |
| 2005/0192189 | A1 | 9/2005 | Wagner et al. |
| 2005/0233935 | A1 | 10/2005 | Gunn et al. |
| 2005/0238680 | A1 | 10/2005 | Stella et al. |
| 2005/0239670 | A1 | 10/2005 | Stella et al. |
| 2005/0276768 | A1 | 12/2005 | Wei et al. |
| 2005/0276829 | A1 | 12/2005 | Stella et al. |
| 2006/0040837 | A1 | 2/2006 | Frantz et al. |
| 2006/0135627 | A1 | 6/2006 | Frantz et al. |
| 2006/0270563 | A1 | 11/2006 | Yang et al. |
| 2006/0270584 | A1 | 11/2006 | Frantz et al. |
| 2008/0095733 | A1 | 4/2008 | Griffin et al. |

FOREIGN PATENT DOCUMENTS

| | | |
|---|---|---|
| EP | 0 719 857 | 6/1988 |
| EP | 0 295 021 | 12/1988 |
| EP | 0 312 234 | 4/1989 |
| EP | 0 346 993 | 12/1989 |
| EP | 0 471 606 | 2/1992 |
| EP | 0 472 089 | 2/1992 |
| EP | 0 504 159 | 9/1992 |
| EP | 0 506 695 | 10/1992 |
| EP | 0 684 982 | 2/1993 |
| EP | 0 530 708 | 3/1993 |
| EP | 0 569 028 | 10/1993 |
| EP | 0 771 188 | 7/1994 |
| EP | 0 419 164 | 11/1994 |
| EP | 0 414 549 | 12/1994 |
| EP | 0 659 205 | 6/1995 |
| EP | 0 430 602 | 9/1995 |
| EP | 0 691 399 | 1/1996 |
| EP | 0 796 614 | 9/1997 |
| EP | 0 796 615 | 9/1997 |
| EP | 0 824 914 | 2/1998 |
| EP | 0 825 200 | 2/1998 |
| EP | 0 839 023 | 5/1998 |
| EP | 0 968 706 | 5/2000 |
| EP | 1 011 625 | 6/2000 |
| EP | 1 027 878 | 8/2000 |
| EP | 0 829 530 | 12/2000 |
| EP | 1 080 714 | 3/2001 |
| EP | 0 586 275 | 3/2004 |
| FR | 2 771 635 | 6/1999 |
| GB | 2 057 533 | 4/1981 |
| GB | 2 292 155 | 2/1996 |
| GB | 2 355 015 | 4/2001 |
| JP | 01-305019 | 12/1989 |
| JP | 02-111713 | 4/1990 |
| JP | 03-291213 | 12/1991 |
| JP | 4-226906 | 8/1992 |
| JP | 04-244009 | 9/1992 |
| JP | 4-327523 | 11/1992 |
| JP | 5-186318 | 7/1993 |
| JP | 7-002677 | 1/1995 |
| JP | 7-509480 | 10/1995 |
| JP | 8-503480 | 4/1996 |
| JP | 8-506328 | 7/1996 |
| JP | 9-020740 | 1/1997 |
| JP | 10-120526 | 5/1998 |
| JP | 10-121030 | 5/1998 |
| JP | 1-305019 | 8/1998 |
| JP | 10-120526 | 12/1998 |
| JP | 2002-528478 | 5/2000 |
| JP | 2001-181153 | 3/2001 |
| JP | 2002-308759 | 10/2002 |
| JP | 2002-541080 | 12/2002 |
| RU | 2 032 726 | 4/1995 |
| WO | WO 94/12151 | 6/1994 |
| WO | WO 96/02224 | 2/1996 |
| WO | WO 96/10625 | 4/1996 |
| WO | WO 97/05857 | 2/1997 |
| WO | WO 97/11145 | 3/1997 |
| WO | WO 98/01171 | 1/1998 |
| WO | WO 98/13022 | 4/1998 |
| WO | WO 99/09947 | 3/1999 |
| WO | WO 99/09948 | 3/1999 |
| WO | WO 99/09950 | 3/1999 |
| WO | WO 99/09951 | 3/1999 |
| WO | WO 99/20243 | 4/1999 |
| WO | WO 99/27907 | 6/1999 |
| WO | WO 00/01347 | 1/2000 |
| WO | WO 00/36079 | 6/2000 |
| WO | WO 00/42985 | 7/2000 |
| WO | WO 00/54749 | 9/2000 |
| WO | WO 00/59454 | 10/2000 |
| WO | WO 00/76460 | 12/2000 |
| WO | WO 01/00778 | 1/2001 |
| WO | WO 01/00779 | 1/2001 |
| WO | WO 01/00780 | 1/2001 |
| WO | WO 01/05932 | 1/2001 |
| WO | WO 01/24807 | 4/2001 |
| WO | WO 01/70193 | 9/2001 |
| WO | WO 01/70926 | 9/2001 |
| WO | WO 01/96461 | 12/2001 |
| WO | WO 02/05758 | 1/2002 |
| WO | WO 02/080477 | 11/2002 |

| | | |
|----|----------------|--------|
| WO | WO 03/055455   | 7/2003 |
| WO | WO 2004/026276 | 4/2004 |
| WO | WO 2004/050055 | 6/2004 |

OTHER PUBLICATIONS

EspaceNet Patent Search Website Family for U.S. Patent No. 4,933,176.

EspaceNet Patent Search Website Family for EP Patent Doc. No. EP 0 824 914.

EspaceNet Patent Search Website Family for EP Patent Doc. No. EP 0 825 200.

International Search Report for International Application No. PCT/US2002/41126.

Gollnick et al., 196(I) "Dermatology Sebaceous Glands, Acne and Related Disorders," pp. 119-157 (1998).

Presentation under confidentiality from Rhodia on Jan. 14, 2004 titled, Structured Liquids and Structured Formulations.

Formula R-0287-191 under confidentiality from Rhodia on Jan. 28, 2004.

Formula R-287-185 & -186 under confidentiality from Rhodia on Feb. 18, 2004.

Formulas R-287-156-1A & -2A under confidentiality from Rhodia on Feb. 18, 2004. 5.

Formula R-287-136 under confidentiality from Rhodia on Feb. 18, 2004.

Formula R-0091-200M under confidentiality from Rhodia on Feb. 18, 2004.

Confidential Letter from Seren Frantz at Rhodia to Peter Haugk at Colgate-Palmolive on 5.

Confidential document for "graniness" observed with Jaguar S from Rhodia on Jul. 11, 2004, 9.

Miracare SLB-365 Material Safety Data Sheet (Jan. 29, 2004).

Miracare SLB-365 Material Safety Data Sheet (Jul. 20, 2004).

Dove Deep Moisture Body Wash Formula from Product Label (undated).

Olay Body Wash Formula from Product Label (undated).

File History U.S. Appl. No. 11/207,238.

File History U.S. Appl. No. 11/668,740.

STABLE SURFACTANT COMPOSITIONS FOR SUSPENDING COMPONENTS

This application claims the benefit under 35 U.S.C. §119 (c) of earlier filed and U.S. Provisional Application No. 60/341,845 filed Dec. 21, 2001 and U.S. Provisional Application No. 60/369,216 filed Apr. 1, 2002, the contents of each of which are incorporated by reference herein.

BACKGROUND OF THE INVENTION

1. Technical Field

This invention relates to aqueous free-flowing compositions. In particular, the invention relates to surfactant compositions that have free-flowing non-Newtonian shear thinning properties and the ability to suspend components.

2. Background of Related Art

It has been documented that free-flowing non-Newtonian shear thinning personal care preparations, comprised of well defined surfactant mixtures, are capable of suspending water-insoluble particles or partially insoluble components, such as vegetable oils, mineral oils, silicone oils, solid particles, abrasives, and similar articles. Examples of such preparations can be found in U.S. Pat. No. 5,556,628 and U.S. Pat. No. 5,965,500, each of which are incorporated by reference herein to the extent they are not inconsistent with this application. These systems provide a means to include otherwise difficult to incorporate components in surfactant mixtures resulting in cosmetic preparations with multi-functional benefits including, in some cases, cleansing, moisturizing, improved skin feel, exfoliation/abrasion, novel appearance, or a combination of these benefits.

The rheological behavior of all surfactant solutions, including liquid personal care solutions, is believed to be dependent on their microstructure, i.e., the shape and concentration of micelles or other self-assembled structures in solutions.

Micelles are not necessarily spherical and may, for example, exist as cylindrical or discoidal micelles. At higher concentrations more ordered liquid crystal phases such as lamellar phases, hexagonal phases or cubic phases may form. Surfactants can take on organized phases above the critical micelle concentration or CMC. (The CMC is defined as the concentration of a surfactant at which it begins to form micelles in solution.) The rheology of the phase is very important when considering the usefulness of a surfactant system.

The rheology of surfactant systems can be described in terms of Newtonian and non-Newtonian viscosities. The rheology of a Newtonian surfactant is described as having a viscosity that is independent of the shear rate (i.e., the system will have the same viscosity as different levels of shear are applied). The rheology of a non-Newtonian surfactant system is described as having a viscosity that is dependent on the shear rate. For a non-Newtonian shear thinning surfactant system, viscosity will be reduced as shear rate is increased. This non-Newtonian rheological behavior effectively allows the suspension of undissolved solids, liquids and gases.

According to U.S. Pat. No. 5,556,628, free flowing non-Newtonian shear thinning cosmetic preparations with good storage stability properties can be prepared utilizing specified surfactant mixtures comprised of an anionic surfactant, sodium lauryl ether sulfate (also known as sodium laureth sulfate) and identified co-surfactants and electrolytes. Experiments confirm that non-Newtonian shear thinning formulations can be prepared following the teachings of U.S. Pat. No. 5,556,628. The subject formulations demonstrate good room temperature (25° C.) and elevated temperature (45° C.) viscosity stabilities. However, such systems may not exhibit optimum performance under all conditions including, but not limited to, freeze/thaw conditions.

Other disclosures suggest the use of fatty acid structurants to stabilize lamellar phase systems (see e.g., U.S. Pat. Nos. 6,150,312, 5,952,286 and 5,962,395). The inherent disadvantage of such systems requiring fatty acid ingredients is that fatty acids form insoluble salts ($Ca^{+2}$ and $Mg^{+2}$ salts) in hard water, which leave an undesirable residue on surfaces such as hair, skin, hard surfaces, etc. This residue is particularly unwanted in shampoo formulations where it will cause dulling of the hair and will act as a foam depressant that negatively impacts high foaming cosmetic formulations such as hair shampoos and body washes.

Moreover, it is difficult to maintain the stability and integrity of other known systems, particularly under freeze/thaw conditions.

Accordingly, it would be desirable to obtain a free flowing non-Newtonian shear thinning composition suitable for use in personal care compositions having the capacity to suspend water-insoluble particles and having stability under freeze/thaw conditions.

SUMMARY OF THE INVENTION

Stable, free flowing cosmetic formulations containing anionic surfactants, electrolytes and alkanolamides, which include long-chain aliphatic hydroxy (or polyhydroxy) amides (hereinafter referred to as long-chain aliphatic acid alkanolamides) or alkoxy long-chain aliphatic hydroxy (or polyhydroxy) amides (hereinafter referred to as alkoxy long-chain aliphatic acid alkanolamides), can be prepared which are ideally suited for the suspension of insoluble particles.

The compositions of the invention may be made by any suitable method for forming a free flowing composition. Electrolyte, surfactant and alkanolamide amounts may be variously adjusted to create a balance that yields the free flowing composition.

The compositions of the invention may be used to suspend agents useful in skin and hair care treatments including, but not limited to, UV absorbers, hair conditioning agents, hair and skin conditioning agents for use in 2 in 1 child care formulations that are tear free, skin conditioning agents, antibacterial agents, styling polymers for hair and skin care formulations (including rinse off applications such as shampoos), conditioning polymers for hair and skin care formulations, precipitated conditioning polymers for enhanced active delivery to hair and skin, conditioning polymers possessing high molecular weights and/or cationic charge densities for hair and skin care formulations, surfactants usually associated with solid formulations (such as cocoyl isethionates), and swellable polymers which hydrate only on application. The compositions of the invention may also be used in the preparation of stable, multi-phase personal care formulations, including those with colored stripes found in body washes, hair shampoos, skin cleansers, child care formulations, facial washes, and skin treatments.

DETAILED DESCRIPTION OF THE INVENTION

The invention relates to surfactant compositions which exhibit non-Newtonian shear thinning behavior (herein referred to as free flowing compositions). These compositions comprise water, at least one anionic surfactant, at least one electrolyte, and at least one alkanolamide. The composition may further comprise water-insoluble particles or partially insoluble components, and/or one or more additional surfactants taken from the categories of anionic surfactants, nonionic surfactants, amphoteric and/or zwitterionic surfactants, and cationic surfactants. The compositions of the present invention are stable compositions, which can suspend difficult to incorporate components and are stable under freeze/thaw conditions.

Without wishing to be bound by theory, the inventors believe that in some examples the compositions of the invention may have a lamellar structure. The compositions of the invention have free-flowing non-Newtonian shear thinning properties and the ability to suspend components (which are known characteristics of lamellar phase surfactant compositions).

The anionic surfactant may be, for example, an aliphatic sulfonate, such as a primary alkane (e.g., $C_8$-$C_{22}$) sulfonate, primary alkane (e.g., $C_8$-$C_{22}$) disulfonate, $C_8$-$C_{22}$ alkene sulfonate, $C_8$-$C_{22}$ hydroxyalkane sulfonate or alkyl glyceryl ether sulfonate (AGS); an aromatic sulfonate such as alkyl benzene sulfonate, or a mixture thereof.

The anionic surfactant may also be an alkyl sulfate (e.g., $C_{12}$-$C_{18}$ alkyl sulfate) or alkyl ether sulfate (including alkyl glyceryl ether sulfates). Preferred among the alkyl ether sulfates are those having the formula:

$$RO(CH_2CH_2O)_nSO_3M \quad \text{(ii)}$$

wherein R is an alkyl or alkenyl having 8 to 18 carbons, typically 12 to 18 carbons; n has an average value typically between 0 and 7, preferably between 0.5 and 3; and M is a solubilizing cation such as sodium, magnesium, potassium, ammonium or substituted ammonium. Lauryl and tridecyl R groups are preferable in some embodiments. The hydrophobic chain may be saturated or unsaturated, straight chain or branched.

The anionic surfactant may also be alkyl sulfosuccinates (including mono- and dialkyl, e.g., $C_6$-$C_{22}$ sulfosuccinates), alkyl and acyl taurates, alkyl and acyl sarcosinates, sulfoacetates, $C_8$-$C_{22}$ alkyl phosphates, alkyl phosphate esters, alkoxyl alkyl phosphate esters, acyl lactates, $C_8$-$C_{22}$ monoalkyl succinates and maleates, and acyl isethionates. Sulfosuccinates may include monoalkyl sulfosuccinates having the formula:

$$R_4O_2CCH_2CH(SO_3M)CO_2M; \quad \text{(iii)}$$

amido-MEA (monoethanolamide) sulfosuccinates of the formula $$R_4CONHCH_2CH_2O_2CCH(SO_3M)CH_2CO_2M \quad \text{(iv)}$$

wherein $R_4$ ranges from $C_8$ to $C_{22}$ alkyl and M is a solubilizing cation; and amido-MIPA (monoisopropanolamide) sulfosuccinates of the formula $$RCONHCH_2CH(CH_3)O_2CCH(SO_3M)CH_2CO_2M \quad \text{(v)}$$

where M is as defined above for formula (ii) and R ranges from $C_8$ to $C_{22}$ alkyl.

Also included as anionic surfactants are the alkoxylated citrate sulfosuccinates and alkoxylated sulfosuccinates such as the following:

$$R-O-(CH_2CH_2O)_nC-CH_2CH(SO_3M)CO_2M \quad \text{(vi)}$$

where M is as defined above for formula (II) and R ranges from $C_{10}$ to $C_{22}$ alkyl.

Sarcosinates are generally indicated by the formula $RCON(CH_3)CH_2CO_2M$, wherein R ranges from $C_8$ to $C_{22}$ alkyl and M is a solubilizing cation.

Taurates are generally identified by the formula:

$$R_2CONR_3CH_2CH_2SO_3M \quad \text{(vii)}$$

wherein $R_2$ ranges from $C_8$ to $C_{22}$ alkyl, $R_3$ ranges from $C_1$ to $C_4$ alkyl, and M is a solubilizing cation.

Another class of anionic surfactants are carboxylates of the following formula:

$$R-O-(CH_2CH_2O)_nCO_2M \quad \text{(viii)}$$

wherein R is $C_8$ to $C_{22}$ alkyl; n is 0 to 20; and M is as defined above in formula (II). Other carboxylates which can be used include amido alkyl polypeptide carboxylates.

Other anionic surfactants which may be used are the $C_8$-$C_{22}$ acyl isethionates. These esters are prepared by reaction of alkali metal isethionate with mixed aliphatic fatty acids having from about 6 to about 22 carbon atoms and an iodine value of less than about 20. At least about 75% of the mixed fatty acids have from about 12 to about 18 carbon atoms and up to about 25% have from about 6 to about 10 carbon atoms.

The acyl isethionate may be an alkoxylated isethionate such as is described in Ilardi et al., U.S. Pat. No. 5,393,466, hereby incorporated by reference to the extent it is consistent with this invention and application. This compound has the general formula:

$$R-\overset{O}{\overset{\|}{C}}-OCH\overset{X}{\underset{|}{{}}}-CH_2-(OCH\overset{Y}{\underset{|}{{}}}-CH_2)_m-SO_3^-M^+ \quad \text{(ix)}$$

wherein R is an alkyl group having 8 to 22 carbons, m is an integer from 1 to 4, X and Y are hydrogen or an alkyl group having 1 to 4 carbons, and $M^+$ is a monovalent cation such as, for example, sodium, potassium or ammonium.

Anionic surfactants with branched alkyl chains such as sodium trideceth sulfate, for example, are preferred in some embodiments. Also, mixtures of anionic surfactants may be used in some embodiments.

The amount of anionic surfactant ingredient is typically about 5% to about 30%, and preferably about 10% to about 20% by weight of the composition.

Except in the examples or where otherwise explicitly indicated, all numbers in this disclosure indicating amounts or ratios of materials or conditions of reactions, physical properties of materials and/or use are understood to be modified by the word "about".

Where weight of a surfactant is utilized in this disclosure, weight is understood to mean weight of active surfactant, with the exception of the examples in the tables.

The electrolyte can be added separately to the composition or it can be included as part of one of the other raw materials. The electrolyte preferably includes an anion comprising phosphate, chloride, sulfate or citrate and a cation comprising sodium, ammonium, potassium, magnesium or mixtures thereof. Some preferred electrolytes are sodium or ammonium chloride and sodium or ammonium sulfate.

The electrolyte should be present in an amount which facilitates formation of the free flowing composition. This amount will typically be from about 0.1% by weight to about 15% by weight, preferably from about 1% to about 6% by weight, but may be varied if required.

Typically, the composition comprises about 3% by weight to about 30% by weight of active surfactants. Frequently, surfactants are sold as solutions in water or other solvents which dilute them to less than 100% active surfactant, therefore the "active surfactant" means actual amount of surfactant delivered to the free flowing composition from a commercial surfactant preparation.

In some embodiments it is desirable that at least one of the components of the composition, such as the anionic surfactant, has an aliphatic chain that has branching or unsaturation or a combination thereof. Branching or branched means that at least one carbon atom of the aliphatic chain is joined to three or four other carbon atoms. Unsaturation means that at least two carbon atoms of the aliphatic chain are joined by a double bond.

The composition also includes at least one alkanolamide having the general structure of:

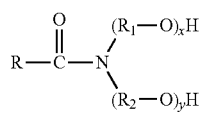

wherein R is $C_8$ to $C_{24}$, or preferably in some embodiments $C_8$ to $C_{22}$, or in other embodiments $C_8$ to $C_{18}$, saturated or unsaturated, straight chain or branched aliphatic groups, $R_1$ and $R_2$ are the same or different $C_2$-$C_4$ straight chain or branched aliphatic groups, x=0 to 10, y=1 to 10, wherein the sum of x and y is less than or equal to 10.

That is, the alkanolamide preferably has a $C_8$ to $C_{24}$ aliphatic chain and the alkanolamide may include one to two alkanol groups which may either have a hydrocarbon backbone or an alkoxy backbone. The hydrocarbon alkanol groups may be $C_2$ to $C_4$ straight chain or branched aliphatic groups. The amount of alkanolamide in the composition is about 0.1% to about 10% by weight, and in some embodiments is preferably about 2% to about 5% by weight. Some preferred alkanolamides include cocamide MEA (coco monoethanolamide) and cocamide MIPA (coco monoisopropanolamide).

The term "alkanolamide" is used collectively hereinafter to include long chain aliphatic acid alkanolamides, alkoxy long-chain aliphatic acid alkanolamides, and mixtures thereof. Further, long-chain aliphatic acid alkanolamides may also be referred to in the art as fatty acid alkanolamides. Alkoxylated is taken to mean an alkanolamide derivatized with $(R_1O)_xH$ wherein $R_1$ is a $C_2$ to $C_4$ straight chain or branched aliphatic group and x is 2 to 10. Examples of free flowing composition formulas are provided in Table 1 below. One advantage of this invention over the previously known formulations is that the composition formulas of the invention do not require a fatty acid structurant as a stabilizer, which in turn may negatively impact the performance of the products.

Additional surfactants from the classes of nonionic surfactants, amphoteric and/or zwitterionic surfactants, and cationic surfactants may optionally be incorporated so as to form a free flowing composition that is capable of suspending water-insoluble particles or partially insoluble components.

Amphoteric and/or zwitterionic surfactants that may be used in this invention preferably include at least one acid group, which may be a carboxylic or a sulphonic acid group. These surfactants include quaternary nitrogen and therefore are quaternary amido acids. They generally include an alkyl or alkenyl group of 7 to 18 carbon atoms and usually comply with the overall structural formula:

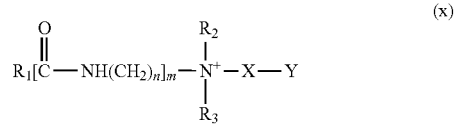

where $R_1$ is alkyl or alkenyl of 7 to 18 carbon atoms; $R_2$ and $R_3$ are each independently hydrogen, alkyl, hydroxyalkyl or carboxyalkyl of 1 to 3 carbon atoms; n is 2 to 4; m is 0 to 1; X is alkylene of 1 to 3 carbon atoms optionally substituted with hydroxyl; and Y is —$CO_2$— or —$SO_3$—.

Suitable amphoteric and/or zwitterionic surfactants within the above general formula include simple betaines of formula:

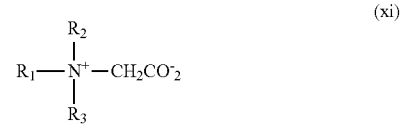

and amido betaines of formula:

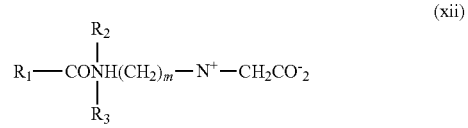

where m is 2 or 3.

In both formulae (xi) and (xii), $R_1$, $R_2$ and $R_3$ are as defined previously in connection with formula (x). $R_1$ may in particular be a mixture of $C_{12}$ and $C_{14}$ alkyl groups derived from coconut so that at least half, preferably at least three quarters, of the $R_1$ groups have 10 to 14 carbon atoms. $R_2$ and $R_3$ are preferably methyl.

A further possibility is that the amphoteric and/or zwitterionic detergent is a sulphobetaine of formula

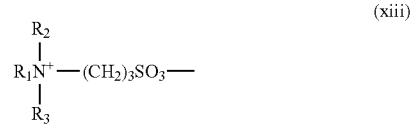

or

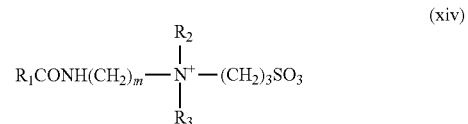

where m is 2 or 3, or variants of these in which —$(CH_2)_3SO_3$ is replaced by

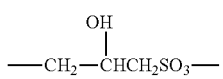

(xv)

In these formulae (xiii), (xiv) and (xv), $R_1$, $R_2$ and $R_3$ are as defined previously in connection with formula (x).

Amphoacetates and diamphoacetates may also be used Amphoacetates generally conform to the following formula:

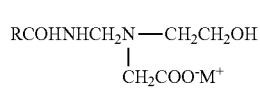

(xvi)

and diamphoacetates generally conform to the following formula:

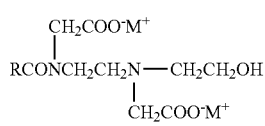

(xvii)

where R is an aliphatic group of 8 to 18 carbon atoms and M is a cation such as sodium, potassium, ammonium, or substituted ammonium. Sodium lauroamphoacetate, sodium cocoamphoactetate, disodium lauroamphoacetate, and disodium cocoamphodiacetate are preferred in some embodiments.

The surfactant system or composition may also optionally include a nonionic surfactant. Nonionic surfactants which may be used include in particular the reaction products of compounds having a hydrophobic group and a reactive hydrogen atom, for example aliphatic alcohols, acids, amides and alkyl phenols, with alkylene oxides, especially ethylene oxide either alone or in combination with propylene oxide. Specific nonionic surfactant compounds include alkyl ($C_6$-$C_{22}$) phenols-ethylene oxide condensates, the condensation products of aliphatic ($C_8$-$C_{18}$) primary or secondary linear or branched alcohols with ethylene oxide, and products made by condensation of ethylene oxide with the reaction products of propylene oxide and ethylenediamine. Other so-called nonionic surfactant compounds include alkyl amine oxides, alkyl amido amine oxides, alkyl tertiary phosphine oxides, dialkyl sulphoxides, aliphatic fatty acid esters of $C_8$-$C_{22}$ alcohols or ethoxylated alcohols, alkoxyl alkyl amines, sorbitan, sorbitan esters and sucrose esters.

The nonionic surfactant may also be a sugar amide, such as a polysaccharide amide. Specifically, the surfactant may be one of the lactobionamides described in U.S. Pat. No. 5,389,279 or one of the sugar amides described in U.S. Pat. No. 5,009,814, both of which are incorporated by reference herein to the extent that they are not inconsistent with this application.

Other surfactants which may be used are those described in U.S. Pat. No. 3,723,325, and alkyl polysaccharide nonionic surfactants as disclosed in U.S. Pat. No. 4,565,647, both of which are also incorporated by reference herein. Preferred alkyl polysaccharides are alkylpolyglycosides of the formula

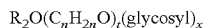

(xvi)

wherein $R_2$ is selected from the group consisting of alkyl, alkylphenyl, hydroxyalkyl, hydroxyalkylphenyl, and mixtures thereof, in which the alkyl groups contain from about 10 to about 18, preferably from about 12 to about 14 carbon atoms; n is from 0 to about 3, preferably 2; t is from 0 to about 10, preferably 0; and x is from about 1.3 to about 10, preferably from about 1.3 to about 2.7. The glycosyl is preferably derived from glucose. To prepare these compounds, the alcohol or alkylpolyethoxy alcohol is formed first and then reacted with glucose, or a source of glucose, to form the glucoside (attachment at the 1-position). The additional glycosyl units can then be attached between their 1-position and the preceding glycosyl unit's 2-, 3-, 4- and/or 6-position, preferably the 2-position.

In some embodiments, the preferred nonionic surfactants include alkoxy fatty acid alcohols or alkypolyglycosides. The amphoteric and/or zwitterionic surfactants preferred in some embodiments include betaines, sultaines, amphoacetates, diamphoacetates or mixtures thereof. The total amount of active nonionic surfactants and amphoteric and/or zwitterionic surfactants is typically about 1% to about 20% and preferably about 3% to about 10% by weight.

The total amount of all surfactants, e.g. anionic surfactants, nonionic surfactants, amphoteric and/or zwitterionic surfactants, and cationic surfactants taken together is typically about 8% to about 30% active surfactant, and preferably about 10% to about 25% active surfactant by weight. In some embodiments it is preferable that at least one of the surfactants has an aliphatic chain that has branching or unsaturation, or a combination thereof.

One embodiment of the invention relates to an aqueous free-flowing composition comprising (a) water, (b) at least one anionic surfactant including a hydrophobe comprised of linear or branched hydrophobic groups, (c) at least one electrolyte (which can either be separately added or included in one of the raw materials) and (d) at least one alkanolamide. The mixture may further comprise water-insoluble particles or partially insoluble components, and/or one or more additional surfactants from the categories of anionic, nonionic, amphoteric, zwitterionic and cationic, or a combination of these.

Surfactants (defined herein as generally referring to surface active agents, including all anionic, nonionic, amphoteric and/or zwitterionic and cationic surface active species and various mixtures thereof) are included in the composition in a combined amount such that the composition exhibits (i) non-Newtonian, shear thinning behavior, (ii) a viscosity equal to or greater than about 3,000 cps as measured at a spindle number 3, speed 6, with a Brookfield LVT viscometer at 25° C. for 30 seconds, and (iii) said viscosity is stable under freeze/thaw conditions without requiring the addition of a separate freeze/thaw stabilizer. Stable is defined herein as a % drop of no more than 40%, preferably no more than 35%, in viscosity measured after at least 1 (one) freeze/thaw cycle, preferably at least 4 (four) freeze/thaw cycles. As used herein, one freeze/thaw cycle is a 24 hour period with 12 hours at −10° C. and 12 hours at 25° C. for the environment immediately surrounding the test sample. In some embodiments the composition may maintain water-insoluble particles or partially insoluble components in suspension.

The compositions of this invention are intended to include all formulations comprised of the surfactant system as described herein, an alkanolamide, an electrolyte, and water. These compositions have free flowing properties capable of suspending a benefit agent(s) and are able to maintain stability under freeze/thaw conditions.

In some embodiments of the present invention it is desirable to include water-insoluble particles or partially insoluble components in the free flowing composition. The terms "water-insoluble particles" and "partially insoluble components" mean solid or non-solid entities which are not completely solubilized in the aqueous medium of the subject composition and include either insoluble or partially soluble species. The terms "water-insoluble particles" and "partially insoluble components" are also understood to mean and encompass those situations where the solid or non-solid entities are present at concentrations above their solubility limit and therefore portions thereof remain undissolved. Typically, the water-insoluble particles or partially insoluble components can be solid particles, liquid ingredients, gases, or mixtures thereof. Some preferred examples of gases include air bubbles. Solid particles could include, for example, solid particles of zinc pyrethione, mica, alumina, silicon pigments, moisturizing beads, natural abrasives, synthetic abrasives (exfoliants) such as polyoxyethylene beads, and apricot seeds. The water-insoluble particles typically have an average particle size from about 0.5 to about 3,000 microns in diameter. The ability to suspend water-insoluble particles or partially soluble components is a desirable feature of the free-flowing non-Newtonian shear thinning liquid composition of the present invention.

Other examples of components that may be suspended by the compositions of the present invention are a number of benefit agents. A "benefit agent" means any active ingredient that is to be delivered into the skin or hair, or onto the skin or hair, or both, at a desired location. The suspended benefit agents may be present in an amount of from about 0 to about 35% by weight of the composition.

More particularly, the suspended benefit agents may include: vegetable oils, including arachis oil, castor oil, cocoa butter, coconut oil, corn oil, cotton seed oil, olive oil, palm kernel oil, rapeseed oil, safflower seed oil, sesame seed oil and soybean oil; esters, including butyl myristate, cetyl palmitate, decyloleate, glyceryl laurate, glyceryl ricinoleate, glyceryl stearate, glyceryl isostearate, hexyl laurate, isobutyl palmitate, isocetyl stearate, isopropyl isostearate, isopropyl laurate, isopropyl linoleate, isopropyl myristate, isopropyl palmitate, isopropyl stearate, propylene glycol monolaurate, propylene glycol ricinoleate, propylene glycol stearate, and propylene glycol isostearate; animal fats, including acetylated lanolin alcohols, lanolin, lard, mink oil and tallow; and fatty acids and alcohols, including behenic acid, palmitic acid, stearic acid, behenyl alcohol, cetyl alcohol, eicosanyl alcohol and isocetyl alcohol.

Other examples of suitable benefit agents include: depigmentation agents; reflectants; UV absorbers, thickening agents; detangling/wet combing agents; film forming polymers; humectants; amino acids and their derivatives; antimicrobial agents; anti-acne agents; anti-aging agents; antiseptics; analgesics; local anesthetics; anti-hair loss agents; hair growth inhibitor agents; inflammation inhibitors; proteins; deodorants and anti-perspirants; agents for treatment of dandruff, seborrheic dermatitis and psoriasis; skin emollients and skin moisturizers; hair conditioners; hair softeners; hair moisturizers; vitamins; tanning agents; skin lightening agents; antifungals such as antifungals for foot preparations; depilating agents; counterirritants; hemorrhoidals; insecticides; pigments or opacifying agents, moisturizing beads, natural abrasives, synthetic abrasives such as polyoxyethylene beads, mineral oils, petrolatum, silicone oils, polyalkylsiloxanes, polyalkyarylsiloxanes, sunscreens and the like; and mixtures thereof.

Examples of suitable reflectants include mica, alumina, calcium silicate, glycol dioleate, glycol distearate, silica, sodium magnesium fluorosilicate, and mixtures thereof.

Examples of suitable UV absorbers include benzophenone, bornelone, PABA (Para Amino Benzoic Acid), butyl PABA, cinnamidopropyl trimethyl ammonium chloride, disodium distyrylbiphenyl disulfonate, potassium methoxycinnamate, and mixtures thereof.

Commercially available thickening agents capable of imparting the appropriate viscosity to the compositions are suitable for use in this invention. Examples of suitable thickening agents include: mono or diesters of polyethylene glycol of the formula:

$$HO-(CH_2CH_2O)_z H \tag{xvii}$$

wherein z is an integer from about 3 to about 200; fatty acids containing from about 16 to about 22 carbon atoms; fatty acid esters of alkoxy polyols; alkoxy derivatives of mono and diesters of fatty acids and glycerine; hydroxyalkyl cellulose; alkyl cellulose; hydroxyalkyl alkyl cellulose; and mixtures thereof. More specifically, suitable thickening agents nonexclusively include, for example, behenalkonium chloride, cetyl alcohol, quaternium 46, PG-hydroxyethyl cellulose, cocodimonium chloride, polyquaternium 6, polyquaternium 7, quaternium 18, PEG-18 glycerol oleate/cocoate, a mixture of acrylates/spirit 50 acrylate copolymer, laureth 3 and propylene glycol, a mixture of cocamidopropylbetaine and glyceryl laurate, a mixture of propylene glycol, PEG 55, and propylene glycol oleate, and mixtures thereof. Preferred thickeners include polyethylene glycol ester, and more preferably PEG-150 distearate.

Suitable detangling/wet combing agents include dioleoylamidoethyl hydroxythylmonium methosulfate, di(soyoylethyl)hydroxyethylmonium methosulfate, hydroxyethyl behenamidopropyl dimonium chloride, olealkonium chloride, polyquaternium 47, stearalkonium chloride, tricetylmonium chloride, guar hydroxypropyltrimonium chloride, hydroxypropyl guar hydroxypropyltrimonium chloride and mixtures thereof.

Suitable film forming polymers include those that, upon drying, produce a substantially continuous coating or film on the hair, skin, or nails. Examples of suitable film forming polymers include acrylamidopropyl trimonium chloride/acrylamide copolymer; corn starch/acrylamide/sodium acrylate copolymer; polyquaternium 10; polyquaternium 47; polyvinylmethyl/maleic anhydride copolymer; styrene/acrylates copolymers; and mixtures thereof.

Commercially available humectants which are capable of providing moisturization and conditioning properties to the composition are suitable for use in the present invention. The humectant is preferably present in an amount of from about 0 percent to about 10 percent, more preferably from about 0.5 percent to about 5 percent, and most preferably from about 0.5 percent to about 3 percent, based on the overall weight of the composition. Examples of suitable humectants include: water soluble liquid polyols such as glycerine, propylene glycol, hexylene glycol, butylene glycol, pentylene glycol, dipropylene glycol, and mixtures thereof; polyalkylene glycols of the formula:

$$HO-(R''O)_b-H \tag{xviii}$$

wherein R" is an alkylene group having from about 2 to about 4 carbon atoms and b is an integer of from about 1 to about 10 (such as PEG 4); polyethylene glycol ethers of methyl glucose having the formula:

$$CH_3-C_6H_{10}O_5-(OCH_2CH_2)_c-OH \tag{xix}$$

wherein c is an integer from about 5 to about 25; urea; fructose; glucose; honey; lactic acid; maltose; sodium glucuronate; and mixtures thereof. In a more preferred embodiment, the humectant is glycerine.

Suitable amino acids which may be beneficial to hair and skin and in some cases can be included as conditioning agents in the compositions of the present invention include amino acids derived from the hydrolysis of various proteins as well as the salts, esters, and acyl derivatives thereof. Examples of such amino acids nonexclusively include amphoteric and/or zwitterionic amino acids such as alkylamido alkylamines; stearyl acetyl glutamate; capryloyl silk amino acids; capryloyl collagen amino acids; capryloyl keratin amino acids; capryloyl pea amino acids; cocodimonium hydroxypropyl silk amino acids; corn gluten amino acids; cysteine; hair keratin amino acids; hair amino acids such as aspartic acid, threonine, scrine, glutamic acid, proline, glycine, alanine, half-cystine, valine, methionine, isoleucine, leucine, tyrosine, phenylalanine, cysteic acid, lysine, histidine, arginine, cysteine, tryptophan, citrulline; other silk amino acids and wheat amino acids; and mixtures thereof.

Suitable proteins which may be beneficial to hair and skin and in some cases can be included as conditioning agents include those polymers that have a long chain, i.e. at least about 10 carbon atoms, and a high molecular weight, i.e. at least about 1000, and are formed by self-condensation of amino acids. Examples of such proteins include collagen, deoxyribonuclease, iodized corn protein, keratin, milk protein, protease, serum protein, silk, sweet almond protein, wheat germ protein, wheat protein, alpha and beta helix of keratin proteins, hair proteins such as intermediate filament proteins, high-sulfur proteins, ultrahigh-sulfur proteins, intermediate filament-associated proteins, high-tyrosine proteins, high-glycine tyrosine proteins, tricohyalin, and mixtures thereof.

Examples of suitable vitamins which may be beneficial to hair and skin and in some cases can be included as conditioning agents include vitamin B complex, including thiamine, nicotinic acid, biotin, pantothenic acid, choline, riboflavin, vitamin B6, vitamin B12, pyridoxine, inositol, carnitine; vitamins A, C, D, E, K and their derivatives, such as vitamin A palmitate; and pro-vitamins, e.g., panthenol (pro vitamin B5), panthenol triacetate and mixtures thereof.

Examples of suitable antibacterial agents for hair and skin care applications include bacitracin, erythromycin, triclosan, neomycin, tetracycline, chlortetracycline, benzethonium chloride, phenol, parachlorometa xylenol (PCMX), triclocarban (TCC), chlorhexidine gluconate (CHG), zinc pyrithione, selenium sulfide and mixtures thereof.

Examples of suitable skin emollients and skin moisturizers include vegetable oils such as arachis oil, castor oil, cocoa butter, coconut oil, corn oil, cotton seed oil, olive oil, palm kernel oil, rapeseed oil, safflower seed oil, sesame seed oil and soybean oil; esters such as butyl myristate, cetyl palmitate, decyloleate, glyceryl laurate, glyceryl ricinoleate, glyceryl stearate, glyceryl isostearate, hexyl laurate, isobutyl palmitate, isocetyl stearate, isopropyl isostearate, isopropyl laurate, isopropyl linoleate, isopropyl myristate, isopropyl palmitate, isopropyl stearate, propylene glycol monolaurate, propylene glycol ricinoleate, propylene glycol stearate, and propylene glycol isostearate; animal fats such as acetylated lanolin alcohols, lanolin, lard, mink oil and tallow; fatty acids and alcohols of behenic acid, palmitic acid, stearic acid, behenyl alcohol, cetyl alcohol, eicosanyl alcohol and isocetyl alcohol.

Additional skin treatment agents and skin conditioning agents include salicylic acid, alpha hydroxy acids, vitamins, vitamin complexes, abrasives, silicones, silicone derivatives, polymers, natural oils, synthetic oils, mineral oils, lanolin, vegetable oils, isostearyl isostearate, glyceryl laurate, methyl gluceth 10, methyl gluceth 20, chitosan, and mixtures thereof.

Examples of suitable hair conditioners include silicones, silicone derivatives, natural oils, synthetic oils, nonionic surfactants, cationic surfactants, waxes, and polymers. Quaternized compounds such as behenamidopropyl PG-dimonium chloride, tricetylammonium chloride, dihydrogenated tallowamidoethyl hydroxyethylmonium methosulfate, and mixtures thereof, as well as lipophilic compounds like cetyl alcohol, stearyl alcohol, hydrogenated polydecene, and mixtures thereof, may also be used.

Examples of suitable hair conditioning polymers include natural and/or synthetic cationic polymers, e.g. quaternized guar, quaternized cellulose, polyquaternium-7 and similar polymers typically at concentrations from about 0.1% to about 3.0% by weight of said composition; natural and/or synthetic nonionic polymers such as alkoxy or propoxylated guar or cellulose, alkyl guar or cellulose, polyethylene glycol, or a mixture of natural and synthetic nonionic polymers typically at concentrations from about 0.1% to about 3.0% by weight of said composition; and polyhydrol moisturizing agents, e.g. glycerine, propylene glycol, sorbitol and similar polymers. Preferable concentrations of polyhydrol moisturizing agents are typically in the range of about 0.2% to about 0.5% by weight of the composition.

Examples of suitable hair softeners include silicone compounds, such as those that are either non-volatile or volatile, or mixtures thereof, and those that are water soluble or water insoluble, or mixtures thereof. Examples of suitable silicones include organo-substituted polysiloxanes, which are either linear or cyclic polymers of silicone/oxygen monomers and which include cetyl dimethicone, cetyl triethylammonium dimethicone copolyol phthalate, cyclomethicone, dimethicone copolyol, dimethicone copolyol lactate, hydrolyzed soy protein/dimethicone copolyol acetate, silicone quaternium 13, stearalkonium dimethicone copolyol phthalate, stearamidopropyl dimethicone, and mixtures thereof.

Examples of suitable hair moisturizers include panthenyl ethyl ether, phytantriol, and mixtures thereof.

Examples of sunscreen agents include butyl methoxydibenzoylmethane, octyl methoxycinnamate, oxybenzone, octocrylene, octyl salicylate, phenylbenzimidazole sulfonic acid, ethyl hydroxypropyl aminobenzoate, menthyl anthranilate, aminobenzoic acid, cinoxate, diethanolamine methoxycinnamate, glyceryl aminobenzoate, titanium dioxide, zinc oxide, oxybenzone, octyl dimethyl PABA (padimate O), red petrolatum, and mixtures thereof.

An example of a suitable tanning agent includes dihydroxyacetone.

Examples of skin lightening agents include hydroquinone, catechol and its derivatives, ascorbic acid and its derivatives, and mixtures thereof.

Examples of suitable insecticides, including insect repellents, anti-scabies and anti-lice treatments, are permethrin; pyrethrin; piperonyl butoxide; imidacloprid; N,N-diethyl toluamide, which refers to the material containing predominantly the meta isomer, i.e., N,N-diethyl-m-toluamide, which is also known as DEET; compounds of the formula:

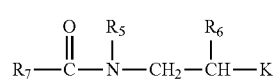

(xx)

wherein $R_5$ is a branched or unbranched alkyl group having from about 1 to about 6 carbon atoms, $R_6$ is H, methyl or ethyl, $R_7$ is a branched or unbranched alkyl or alkoxy group having from about 1 to about 8 carbon atoms, and K is a —CN or a —COOR$_8$ group, wherein R$_8$ is a branched or unbranched alkyl group having from about 1 to about 6 carbon atoms; natural or synthetic pyrethroids, whereby the natural pyrethroids are contained in pyrethrum; the extract of the ground flowers of *Chrysanthemum cinerariaefolium* or *Chrysanthenum coccineum*; and mixtures thereof. Within the structure of Formula (xx) are ethyl 3-(N-butylacetamido) propionate, wherein R$_7$ is a CH$_3$ group, R$_5$ is an n-butyl group, R$_6$ is H, K is COOR$_8$ and R$_8$ is ethyl.

An example of an antifungal for foot preparations includes tolnaftate.

Examples of suitable depilating agents include calcium thioglycolate, magnesium thioglycolate, potassium thioglycolate, strontium thioglycolate, and mixtures thereof.

Examples of suitable external analgesics and local anesthetics include benzocaine, dibucaine, benzyl alcohol, camphor, capsaicin, capsicum, capsicum oleoresin, juniper tar, menthol, methyl nicotinate, methyl salicylate, phenol, resorcinol, turpentine oil, and mixtures thereof.

Examples of suitable antiperspirants and deodorants include aluminum chlorohydrates, aluminum zirconium chlorohydrates, and mixtures thereof.

Examples of suitable counterirritants include camphor, menthol, methyl salicylate, peppermint oils, clove oils, ichtammol, and mixtures thereof.

An example of a suitable inflammation inhibitor is hydrocortisone.

Examples of suitable hemorrhoidal products include anesthetics such as benzocaine, pramoxine hydrochloride, and mixtures thereof; antiseptics such as benzethonium chloride; astringents such as zinc oxide, bismuth subgallate, balsam Peru, and mixtures thereof; skin protectants such as cod liver oil, vegetable oil, and mixtures thereof.

Examples of suitable benefit agents having therapeutic components that are effective in the treatment of dandruff, seborrheic dermatitis, and psoriasis, as well as the symptoms associated therewith, include zinc pyrithione; shale oil and derivatives thereof such as sulfonated shale oil; selenium sulfide; sulfur; salicylic acid; coal tar; povidone-iodine; imidazoles such as ketoconazole, dichlorophenyl imidazolodioxalan, clotrimazole, itraconazole, miconazole, climbazole, tioconazole, sulconazole, butoconazole, fluconazole; miconazolenitrite and any possible stereo isomers and derivatives thereof such as anthralin; piroctone olamine (Octopirox); selenium sulfide; ciclopirox olamine; anti-psoriasis agents such as vitamin D analogs, e.g. calcipotriol, calcitriol, and tacaleitrol; vitamin A analogs such as esters of vitamin A including vitamin A palmitate, retinoids, retinols, and retinoic acid; corticosteroids such as hydrocortisone, clobetasone, butyrate, clobetasol propionate; and mixtures thereof.

Some preferred benefit agents for treatment of dandruff, seborrheic dermatitis, and psoriasis, as well as the symptoms associated therewith, include sulfonated shale oil, elubiol, 6-(1-piperidinyl)-2-4-pyrimidinediamine-3-oxide, finasteride, ketoconazole, salicylic acid, zinc pyrithione, coal tar, benzoyl peroxide, selenium sulfide, hydrocortisone, sulfur, menthol, praxomine hydrochloride, tricetylammonium chloride, polyquaternium 10, panthenol, panthenol triacetate, vitamin A and derivatives thereof, vitamin B and derivatives thereof, vitamin C and derivatives thereof, vitamin D and derivatives thereof, vitamin E and derivatives thereof, vitamin K and derivatives thereof, keratin, lysine, arginine, hydrolzed wheat proteins, hydrolyzed silk proteins, octyl methoxycinnamate, oxybenzone, minoxidil, titanium dioxide, zinc dioxide, retinol, erythromycin, tretinoin, and mixtures thereof.

Examples of benefit agents suitable for treating hair loss include, but are not limited to, potassium channel openers or peripheral vasodilators such as minoxidil, diazoxide, and compounds such as N"-cyano-N-(tert-pentyl)-N'-3-pyridinyl-guanidine ("P-1075") as disclosed in U.S. Pat. No. 5,244,664, which is incorporated by reference herein; vitamins, such as vitamin E and vitamin C, and derivatives thereof such as vitamin E acetate and vitamin C palmitate; hormones such as erythropoietin; prostaglandins, such as prostaglandin EI and prostaglandin F2-alpha; fatty acids such as oleic acid; diuretics such as spironolactone; heat shock proteins ("HSP"), such as HSP 27 and HSP 72; calcium channel blockers, such as verapamil HCL, nifedipine, and diltiazemamiloride; immunosuppressant drugs, such as cyclosporin and Fk-506; 5 alpha-reductase inhibitors such as finasteride; growth factors such as EGF, IGF and FGF; transforming growth factor beta; tumor necrosis factor; non-steroidal anti-inflammatory agents such as benoxaprofen; retinoids and derivatives thereof such as tretinoin; cytokines, such as IL-6, IL-1 alpha, and IL-1 beta; cell adhesion molecules such as ICAM; glucocorticoids such as betamethasone; botanical extracts such as aloe, clove, ginseng, rehmannia, swertia, sweet orange, zanthoxylum, *Serenoa repens* (saw palmetto), *Hypoxis rooperi*, stinging nettle, pumpkin seeds, and rye pollen; other botanical extracts including sandalwood, red beet root, chrysanthemum, rosemary, burdock root and other hair growth promoter activators as disclosed in DE 4330597, which is incorporated by reference herein to the extent that it is not inconsistent with the present application; homeopathic agents such as Kalium Phosphoricum D2, Azadirachta indica D2, and Joborandi DI; genes for cytokines, growth factors, and male-pattern baldness; antifungals such as ketoconazole and elubiol; antibiotics such as streptomycin; protein inhibitors such as cycloheximide; acetazolamide; benoxaprofen; cortisone; diltiazem; hexachlorobenzene; hydantoin; nifedipine; penicillamine; phenothiazines; pinacidil; psoralens; verapamil; zidovudine; alpha-glucosylated rutin having at least one rutin selected from quercetin, isoquercitrin, hesperidin, naringin, and methylhesperidin; and flavonoids and transglycosidated derivatives thereof which are all disclosed in JP 7002677, which is incorporated by reference herein to the extent that it is not inconsistent with the present application; and mixtures thereof.

Examples of benefit agents suitable for use in inhibiting hair growth include serine proteases such as trypsin; vitamins such as alpha-tocopherol (vitamin E) and derivatives thereof such as tocopherol acetate and tocopherol palmitate; antineoplastic agents, such as doxorubicin, cyclophosphamide, chlormethine, methotrexate, fluorouracil, vincristine, daunorubicin, bleomycin and hydroxycarbamide; anticoagulants, such as heparin, heparinoids, coumaerins, detran and indandiones; antithyroid drugs, such as iodine, thiouracils and carbimazole; lithium and lithium carbonate; interferons, such as interferon alpha, interferon alpha-2a and interferon alpha-2b; retinoids, such as retinol (vitamin A), isotretinoin; glucocorticoids such as betamethasone, and dexamethosone; antihyperlipidaemic drugs, such as triparanol and clofibrate; thallium; mercury; albendazole; allopurinol; amiodarone; amphetamines; androgens; bromocriptine; butyrophenones; carbamazepine; cholestyramine; cimetidine; clofibrate; danazol; desipramine; dixyrazine; ethambutol; etionamide; fluoxetine; gentamicin; gold salts; hydantoins; ibuprofen; imipramine; immunoglobulins; indandiones; indomethacin; intraconazole; levadopa; maprotiline; methysergide; metoprolol; metyrapone; nadolol; nicotinic acid; potassium thiocyanate; propranolol; pyridostimine; salicylates; sulfasalazine; terfenadine; thiamphenicol; thiouracils; trimethadione; troparanol; valproic acid; and mixtures thereof.

Examples of suitable anti-aging agents include inorganic sunscreens such as titanium dioxide and zinc oxide; organic sunscreens such as octyl-methyl cinnamates and derivatives thereof; retinoids; vitamins such as vitamin E, vitamin A, vitamin C, vitamin B, and derivatives thereof such as vitamin E acetate, vitamin C palmitate, and the like; antioxidants including beta carotene, alpha hydroxy acid such as glycolic acid, citric acid, lactic acid, malic acid, mandelic acid, ascorbic acid, alpha-hydroxybutyric acid, alpha-hydroxyisobutyric acid, alpha-hydroxyisocaproic acid, atrolactic acid, alpha-hydroxyisovaleric acid, ethyl pyruvate, galacturonic acid, glucoheptonic acid, glucopheptono 1,4-lactone, gluconic acid, gluconolactone, glucuronic acid, glucuronolactone, glycolic acid, isopropyl pyruvate, methyl pyruvate, mucic acid, pyruvic acid, saccharic acid, saccharic acid 1,4-lactone, tartaric acid, and tartronic acid; beta hydroxy acids such as beta-hydroxybutyric acid, beta-phenyl-lactic acid, beta-phenylpyruvic acid; botanical extracts such as green tea, soy, milk thistle, algae, aloe, angelica, bitter orange, coffee, goldthread, grapefruit, hoellen, honeysuckle, Job's tears, lithospermum, mulberry, peony, puerarua, rice, safflower, and mixtures thereof.

Some preferred anti-aging agents comprise retinoids including retinol and tretinoin, anti-oxidants, alpha-hydroxy acids and beta-hydroxy acids.

Examples of suitable anti-acne agents include, but are not limited to, topical retinoids including tretinoin, isotretinoin, motretinide, adapalene, tazarotene, azelaic acid, retinol; salicylic acid; benzoyl peroxide; resorcinol; antibiotics such as tetracycline and isomers thereof, erythromycin; anti-inflammatory agents such as ibuprofen, naproxen, hetprofen; botanical extracts such as alnus, arnica, artemisia capillaris, asiasarum root, birth or afterbirth, calendula, chamomile, cnidium, comfrey, fennel, galla rhois, hawthron, houttuynia, hypericum, jujube, kiwi, licorice, magnolia, olive, peppermint, philodendron, salvia, sasa albomarginata; imidazoles such as ketoconazole and elubiol; those anti-acne agents described in Gollnick, H. et al. 196(I) Dermatology Sebaceous Glands, Acne and Related Disorders, 119-157 (1998), which is incorporated by reference herein to the extent that it is not inconsistent with the present application; and mixtures thereof.

Examples of suitable depigmentation agents include retinoids such as retinol; kojic acid and its derivatives such as, for example, kojic dipalmitate; hydroquinone and its derivatives such as arbutin; transexamic acid; vitamins such as niacin, vitamin C and its derivatives; azelaic acid; placertia; licorice; extracts such as chamomile and green tea; and mixtures thereof. Retinol, kojic acid, and hydroquinone are preferred.

Other examples of benefit agents include allergy inhibitors, anti-wrinkling agents, anti-pruritics, antitussives, hair growth promoting agents, antihistamines, anticholinergics, antiemetics, antiinfectives, vasoconstrictors, vasodilators, wound healing promoters, peptides, polypeptides, medicament agents, shaving preparations, poison ivy products, poison oak products, burn products, anti-diaper rash agents, prickly heat agents, herbal extracts, retinal, flavoides, sensates, skin conditioners, hair lighteners, cell turnover enhancers and the like, and mixtures thereof.

Other components that may be added to the compositions include typical components added to personal care products, all of which are useful in enhancing the appearance or cosmetic properties of the product. These may include, for example, auxiliary thickeners such as carboxymethylcellulose, magnesium aluminum silicate, hydroxyethylcellulose, methylcellulose, carbopols, glucamides; sequestering agents such as tetrasodium ethylenediaminetetraacetate ($Na_4$-EDTA), EHDP or mixtures thereof, which can be present in varying amounts including amounts ranging from about 0.01 to about 5%, preferably about 0.01% to about 3%; and coloring agents, pigments, perfumes, opacifiers and pearlizers such as zinc stearate, magnesium stearate, $TiO_2$, EGMS (ethylene glycol monostearate) and Lytron 621 (Styrene/Acrylate copolymer).

Inclusion of antimicrobials may be used advantageously in some embodiments. Such antimicrobials include, for example, 2-hydroxy-4,2'4' trichlorodiphenylether (DP300); preservatives such as dimethyloldimethylhydantoin (Glydant XL1000), parabens, sorbic acid, etc.; antioxidants such as, for example, butylated hydroxytoluene (BHT), and mixtures thereof.

The compositions of the invention may be made by any suitable method for forming a free flowing composition. The amounts of electrolyte, surfactant, and alkanolamide may be variously adjusted to create a balance that yields the free flowing non-Newtonian shear thinning composition of the present invention.

The free-flowing non-Newtonian shear thinning compositions of the present invention may, in some embodiments, function as a delivery system. The amount of benefit agent to be combined with the composition of the invention may vary depending upon, for example, the resulting benefit desired and the sensitivity of the user to the benefit agent. Unless otherwise specified, typically the benefit agent is present in a personal care product in an amount, based upon the total weight of the free-flowing non-Newtonian shear thinning composition, from about 0.001% to about 20%. In a preferred embodiment, the benefit agent is present in an amount ranging from about 0.001% to about 10% of the composition, with a range from about 0.001% to about 5% being most preferred. While it is expected that one or more benefit agents may be used in a composition, the choice of benefit agent(s) to include will depend upon the intended end use of the composition and the mutual compatibility of the benefit agents selected.

The compositions of the invention may also be used to prepare shampoos and conditioners, skin cleansing preparations, compositions for delivering cosmetic preparations or topical therapeutic agents, and the like.

The compositions of the invention may be used to suspend agents useful in skin and hair care treatments including, but not limited to, UV absorbers, hair conditioning agents, hair and skin conditioning agents for use in child care formulations including tear free shampoos and baby baths, skin conditioning agents, anti-bacterial agents, styling polymers for hair and skin care formulations (including rinse off applications such as shampoos), conditioning polymers for hair and skin care formulations, precipitated conditioning polymers for enhanced active delivery to hair and skin, conditioning polymers possessing high molecular weights and/or cationic charge densities for hair and skin care formulations, surfactants usually associated with solid formulations (such, as cocoyl isethionates), and swellable polymers which hydrate only on application. The compositions of the invention may also be used in the preparation of stable, multi-phase personal care formulations, including those with colored stripes found in body washes, hair shampoos, skin cleansers, child care formulations including tear free shampoos, children's conditioning shampoos and baby baths, facial washes, and skin treatments.

In embodiments wherein the composition of the invention containing a benefit agent is used as a shampoo, the shampoo is applied to wet hair, then the hair is washed in accordance with known practices. More preferably, the composition remains on the hair from about 0 to about 10 minutes, and preferably from about 1 to about 5 minutes before rinsing.

The following nonlimiting examples are illustrative of the broad range of free-flowing non-Newtonian shear thinning compositions that may be prepared and used in accordance with the present invention.

Example 1

Exemplary Compositions

Table 1 provides seven illustrative examples of compositions of the present invention (#1-7) having non-Newtonian shear thinning behaviors. It should be noted that the percentages given without parentheses are amounts of commercial material added and the values in parentheses are the amounts of active ingredient added.

The compositions of Table 1 include illustrative examples in which oil, emollient or appearance modifiers have been included. These examples are provided as representative examples and are not intended to limit the inclusion of a particular additive to a particular composition nor to imply that only a single additive may be included. Indeed, inclusion of multiple kinds of water insoluble materials, particles, benefit agents, other optional ingredients, or mixtures thereof may be desirable in some embodiments.

TABLE I

| | | 1 | 2 | 3 | 4 | 5 | 6 | 7 |
|---|---|---|---|---|---|---|---|---|
| Empicol ESB-70 (Rhodia) | 70% Active Sodium Laureth Sulfate | 8.15 (5.70)$^{(1)}$ | | | | | | |
| Rhodapex EST-30 (Rhodia) | 30% Active Sodium Trideceth Sulfate | | 48.50 (14.55) | 48.50 (14.55) | | 47.4 | 53.2 | 53.2 |
| Empicol BSD-52 (Albright & Wilson) Laureth Sulfate | 52% Active Sodium/Magnesium | | | | 28.30 (14.72) | | | |
| Empilan CIS (Albright & Wilson) | Cocamide MIPA | 2.60 | | 3.00 | 3.90 | — | — | — |
| Alkamide C-4 (Rhodia) | PEG-5 Cocamide | | | | | 2.9 | — | — |
| Alkamide C-212 (Rhodia) | Cocamide MEA | 3.00 | | | | — | 5.0 | 5.0 |
| Miranol Ultra L-32 (Rhodia) | 32% Active Sodium Lauroamphoacetate | | 15.00 (4.8) | 15.00 (4.8) | | 14.5 | — | — |
| Water | | | | | | 24.9 | 36.5 | 36.5 |
| Empigen BB (Albright & Wilson) | Lauryl Betaine | 0.70 (0.21) | | | 13.00 (3.9) | | | |
| Laureth-2 | | 1.50 | | | 3.00 | | | |
| Glycerine | | | 1.00 | | | | | |
| Jaguar C-17 (Rhodia) | Guar Hydroxypropyltrimonium Chloride | | 0.50 | 0.50 | | | | |
| Sodium Chloride | | 12.40 (12.00) | 3.00 | 3.00 | 16.20 (15.55) | 8.6 | 5.0 | 5.0 |
| Citric Acid (to pH 4.0-6.5) | | | Q.S. | Q.S. | | | | |
| Citric Acid, 50% | | | | | | 1.7 | 0.3 | 0.3 |
| Sunflower Oil | | | 6.67 | | | | | |
| Petrolatum | | | 3.33 | | | | | |
| Silbione 47V60,000 | | | | | 3.00 | | | |
| TiO$_2$ | | | | | 0.50 | | | |
| Mica | | 1.00 | | | | | | |
| Lipo Pearl | Vera & Mineral Oil | | | | | 1.00 | | |
| Appearance | | Opaque Liquid | White Lotion | White Lotion | Opaque Liquid | | | |
| Sample Temperature for Viscosity | | | | | | 24° C. | 23° C. | 23° C. |
| Initial Viscosity (X1000) cPs | | 7.7 | 152 | 120 | 16.7 | 8.5 | 10.7 | 10.3 |
| Viscosity after 4 days F/T (X1000) cPs | | | | | | 8.5 | | |

TABLE I-continued

|  | 1 | 2 | 3 | 4 | 5 | 6 | 7 |
|---|---|---|---|---|---|---|---|
| Viscosity after 5 days F/T (X1000) cPs |  |  |  |  |  | 9.6 | 9.7 |
| Viscosity After F/T Cycle (X1000) cPs |  | 7.8 | 160 | 119 | 16.6 |  |  |

[1] values given in parentheses are amounts of active ingredient

Example 2

Formulations and Testing of Alkoxy Alkanolamide Compositions

Alkoxy Alkanolamide (PEG-5 Cocamide, Alkamide® C-4) was used to create a structured liquid formulation with sodium trideceth sulfate, sodium lauroamphoacetate, and sodium chloride. The base formulation of this composition is provided in Table 2.

TABLE 2

| Component | wt (g) | w/w % | % Act |
|---|---|---|---|
| Rhodapex EST30 | 686 | 50.81 | 15.0 |
| Miranol Ultra L-32 | 210 | 15.56 | 4.9 |
| Alkamide C-4 (PEG-5 cocamide) | 42 | 3.11 | 3.1 |
| Water | 360.8 | 26.73 |  |
| 50% Citric Acid | 24.2 | 1.79 |  |
| Sodium Chloride | 27 | 2.00 |  |
|  | 1350 g | 100.00% | 23.0 pH = 6.08 |

A series of samples with various salt concentrations relative to the amount of base formulation of Table 2 were prepared and tested. The compositions of the tested samples are provided below in Table 3.

TABLE 3

| Sample | % Rhodapex EST30 | % Miranol Ultra L-32 | % Alkamide C-4 | % NaCl added | % water/inerts |
|---|---|---|---|---|---|
| 8-1 | 50.8 | 15.6 | 3.1 | 2.0 | 28.5 |
| 8-2 | 50.3 | 15.4 | 3.1 | 3.0 | 28.2 |
| 8-3 | 49.8 | 15.2 | 3.0 | 4.0 | 28.0 |
| 8-4 | 49.3 | 15.1 | 3.0 | 4.9 | 27.7 |
| 8-5 | 48.8 | 14.9 | 3.0 | 5.9 | 27.4 |
| 8-6 | 48.3 | 14.9 | 3.0 | 6.8 | 27.1 |
| 8-7 | 47.8 | 14.6 | 2.9 | 7.7 | 26.9 |
| 8-8 | 47.4 | 14.5 | 2.9 | 8.6 | 26.6 |
| 8-9 | 46.9 | 14.4 | 2.9 | 9.5 | 26.3 |

Viscosities were measured for each of these exemplary compositions before and after 4 days of freeze/thaw. The viscosity was measured at LVT#3, 25° C., 6 RPM, 0.5 min. Appearance was determined visually by observing the presence of air bubbles and sustaining the air bubbles in the suspended state before and after the freeze/thaw cycle. Only samples that were one phase in the initial centrifuge test were measured. The results, set forth below in Table 4, indicate that adding at least 8.5% NaCl to the composition provided a stable formulation. As used herein, "structure" or "structured" means a system that appears shear thinning.

TABLE 4

| Sample | Viscosity Before F/T | Viscosity After F/T | Appearance Structured? |
|---|---|---|---|
| 8-4 | 4,680 | — | No |
| 8-5 | 7,760 | — | No |
| 8-6 | 11,500 | 4,600 | Yes |
| 8-7 | 13,000 | 7,900 | Yes |
| 8-8 | 8,540 | 8,500 | Yes |
| 8-9 | 8,440 | 8,860 | Yes |

Example 3

Formulations without Amphoteric and/or Zwitterionic Surfactant

Compositions containing sodium trideceth sulfate, sodium chloride, and either cocamide MEA or cocamide MIPA were tested for visual structured appearance and freeze/thaw viscosity loss. An amphoteric surfactant was not used in these formulations. The exemplary base formulations used for these compositions are provided in Tables 5 and 6 below.

TABLE 5

Base Formulation 9-1
Cocamide MIPA (Empilan CIS)

| Component | wt (g) | w/w % | % Act |
|---|---|---|---|
| Rhodapex EST30 | 278.7 | 54.63 | 16.1 |
| Empilan CIS | 26 | 5.10 | 5.1 |
| Water | 191.3 | 37.49 |  |
| 50% Citric Acid | 1.70 | 0.33 |  |
| Sodium Chloride | 12.5 | 2.45 |  |
|  | 510.2 g | 100.00% | 21.2 pH = 5.4 |

TABLE 6

Base Formulation 9-2
Cocamide MEA (Alkamide C-212)

| Component | wt (g) | w/w % | % Act |
|---|---|---|---|
| Rhodapex EST30 | 278.7 | 54.63 | 16.1 |
| Alkamide C-212 | 26 | 5.10 | 5.1 |
| Water | 191.3 | 37.50 |  |
| 50% Citric Acid | 1.64 | 0.32 |  |
| Sodium Chloride | 12.5 | 2.45 |  |
|  | 510.14 g | 100.00% | 21.2 pH = 5.6 |

A series of samples based upon each of the base formulations described above in Tables 5 and 6, respectively, were prepared with various salt concentrations relative to the amount of base formulation. Exemplary compositions were prepared, the formulations of which are shown in Tables 7 and 8 below.

TABLE 7

| Sample | % Rhodapex EST30 | % Empilan CIS | % NaCl added | % water/inerts |
|---|---|---|---|---|
| 9-1-1 | 54.6 | 5.1 | 2.5 | 37.8 |
| 9-1-2 | 53.8 | 5.0 | 4.0 | 37.2 |
| 9-1-3 | 53.2 | 5.0 | 5.0 | 36.8 |
| 9-1-4 | 52.7 | 4.9 | 5.9 | 36.5 |
| 9-1-5 | 52.1 | 4.9 | 6.9 | 36.1 |
| 9-1-6 | 51.6 | 4.8 | 7.8 | 35.8 |

TABLE 8

| Sample | % Rhodapex EST30 | % Alkamide C-212 | % NaCl added | % water/inerts |
|---|---|---|---|---|
| 9-2-1 | 54.6 | 5.1 | 2.5 | 37.8 |
| 9-2-2 | 53.8 | 5 | 4 | 37.2 |
| 9-2-3 | 53.2 | 5 | 5 | 36.8 |
| 9-2-4 | 52.7 | 4.9 | 5.9 | 36.5 |
| 9-2-5 | 52.1 | 4.9 | 6.9 | 36.1 |
| 9-2-6 | 51.6 | 4.8 | 7.8 | 35.8 |

The viscosity of these compositions before and after 5 days of freeze/thaw was measured in accordance with the procedures described above in Example 2. The results are set forth below in Table 9. As Table 9 shows, freeze/thaw viscosities and appearance data for the compositions of Tables 7 and 8 indicate that, for these compositions, a stable composition could be obtained with the addition of 5% or greater sodium chloride.

TABLE 9

| Sample | Initial appearance | Initial Viscosity | F/T Viscosity | Appearance Structured? |
|---|---|---|---|---|
| 9-1-1 | 25% clear | — | — | — |
| 9-1-2 | 1-phase | 11,800 | 1,540 | No |
| 9-1-3 | 1-phase | 10,280 | 9,700 | Yes |
| 9-1-4 | 1-phase | 9,660 | 11,300 | Yes |
| 9-1-5 | 1-phase | 9,480 | 11,760 | Yes |
| 9-1-6 | 1-phase | 6,000 | 9,200 | Yes |
| 9-2-1 | 15% clear | — | — | — |
| 9-2-2 | 1-phase | 13,360 | 3,000 | No |
| 9-2-3 | 1-phase | 10,720 | 9,600 | Yes |
| 9-2-4 | 1-phase | 9,460 | 11,900 | Yes |
| 9-2-5 | 1-phase | 8,000 | 12,200 | Yes |
| 9-2-6 | 1-phase | 2,300 | 10,400 | Yes |

Example 4

Formulations and Testing of Increasing Levels of Alkanolamide

Alkamide® C-212 (cocamide MEA) was used to create a structured liquid composition with sodium trideceth sulfate, sodium lauroamphoacetate, and sodium chloride. The formulations of exemplary compositions are provided in Table 10 below.

TABLE 10

| Sample | % Rhodapex EST30 | % Alka-mide C-212 | % Miranol Ultra L-32 | % NaCl | % water | pH after citric acid |
|---|---|---|---|---|---|---|
| 10-1 | 47.6 | 0 | 14.7 | 2.0 | 35.7 | 5.8 |
| 10-2 | 47.6 | 1.0 | 14.7 | 2.0 | 33.8 | 5.8 |
| 10-3 | 47.6 | 2.0 | 14.7 | 2.0 | 32.8 | 5.88 |
| 10-4 | 47.6 | 2.9 | 14.7 | 2.0 | 31.8 | 5.82 |
| 10-5 | 47.6 | 3.9 | 14.7 | 2.0 | 30.8 | 5.75 |
| 10-6 | 47.6 | 4.9 | 14.7 | 2.0 | 29.9 | 5.9 |
| 10-7 | 47.6 | 5.9 | 14.7 | 2.0 | 28.9 | 5.86 |

The viscosity was measured before and after one day of freeze/thaw in accordance with the procedures set forth in Example 2 and the results are summarized below in Table 11. As Table 11 shows, freeze/thaw viscosities (1 day) and appearance data for the compositions of Table 10 indicate that, for the examples tested, a stable composition could be obtained with 3% or greater added cocamide MEA.

TABLE 11

| Sample | Viscosity Before F/T | Viscosity After F/T | Appearance |
|---|---|---|---|
| 10-1 | 800 | 400 | 75% hazy |
| 10-2 | 3,400 | 3,600 | Hazy |
| 10-3 | 3,800 | 4,100 | Hazy |
| 10-4 | 5,900 | 6,400 | Incr. Opacity |
| 10-5 | 7,500 | 7,100 | Incr. Opacity |
| 10-6 | 8,700 | 9,000 | Incr. Opacity |
| 10-7 | 11,000 | 11,500 | Incr. Opacity |

Example 5

Preparation of Compositions

Methods for the preparation of compositions having non-Newtonian shear thinning behavior may be varied according to the physical features of a particular composition.

An exemplary method for preparing lower viscosity systems incorporating solid agents such as compositions 1 and 4 of Table 1 is as follows: all of the surface active agents (i.e. surfactants), including the alkanolamide, were added to the water with moderate agitation while stirring. When solid surfactants were used, the mixtures were heated to a minimum of about 5-10° C. above the melting temperature of the solid surfactant. The mixtures were stirred until they become homogenous and, when heating was used, stirring was continued until the mixture cooled to ambient temperature. The pH was then adjusted to about 5.5 to 6.5 and the electrolyte and solid benefit agent were added with stirring to disperse.

An exemplary method for incorporating emollients into higher viscosity systems such as compositions 2 and 3 of the table set forth in Table 1 is as follows. Cationic polymer was first added to water. This was accomplished either by pre-solubilization of the cationic polymer in glycerine or adding the cationic polymer directly to the water and adjusting the pH to 4-5. Anionic surfactants, and any co-surfactants or ingredients (other than any amphoteric and/or zwitterionic surfactants and alkanolamides) were added and the mixture was heated to about 65-80° C., e.g. a temperature greater than the melting point of the alkanolamide used. The alkanolamide was then added and the composition was mixed at a mixing speed of 200-400 RPM, utilizing an overhead mechanical stirrer with a stir shaft that includes (2) two impellers each with four pitched blades, the point of each blade being more strongly pitched than the center portion and the point of each blade alternating in an up and down pattern. A temperature at a minimum of 5-10° C. above the melting point of the alkanolamide was maintained until the system was homogeneous. The emollient was heated to about 60-65° C. and added to the surfactant mixture once the surfactant mixture reached approximately the same temperature, i.e., about 60-65° C. The mixture was then cooled to 30-35° C. and the amphoteric and/or zwitterionic surfactant, if used, was added at the beginning of this cooling process. When a temperature of 30-35° C. was reached, the pH was adjusted with citric acid, and heat sensitive additives such as color, fragrance, and preservatives, for example, as well as the electrolyte, were added. Mixing was continued for a minimum of 1-2 hours after the addition of electrolyte. A total 500 g to 1000 g was made per batch.

Those persons skilled in the art will appreciate that the present invention is susceptible to a broad utility and application. Many embodiments and adaptations of the invention, including various methods for preparing the composition of the present invention other than those herein described, as well as many variations and modifications, will be apparent from or reasonably suggested by the present invention and the foregoing description thereof, without departing from the substance or scope of the present invention. Accordingly, while the present invention has been described herein in detail in exemplary embodiments, it is to be understood that this disclosure is only illustrative and exemplary of the present invention and is made merely for purposes of providing a full and enabling disclosure of the invention. The foregoing is not intended or to be construed to limit the present invention or otherwise to exclude any such other embodiments, adaptations, variations, modifications, the present invention being limited only by the claims appended hereto and the equivalents thereof.

What is claimed is:

1. A composition comprising:
   (a) about 5% to about 30% by weight of sodium trideceth sulfate;
   (b) about 1% to about 20% by weight of at least one material comprising lauroamphoacetate or cocoamidopropyl betaine;
   (c) about 0.1% to about 10% by weight of cocomonoethanolamide;
   (d) water;
   (e) about 0.1% to about 3% by weight of guar hydroxypropyl trimonium chloride;
   (f) about 0% to about 35% by weight of an oil phase; and
   (g) salt.

2. The composition of claim 1, wherein in (b) the material comprises lauroamphoacetate.

3. The composition of claim 1, wherein the pH of the composition is about 4.0 to about 6.5.

4. The composition of claim 1 further comprising about 0.1% to about 3.0% by weight of a nonionic guar gum.

5. The composition of claim 1 wherein the oil phase comprises an oil comprising a vegetable, mineral, or silicone oil.

6. The composition of claim 1, wherein said composition comprises a total salt content of about 1% to about 6% by weight.

7. The composition of 1 wherein the salt is NaCl.

8. The composition of 5 wherein the vegetable oil comprises sunflower oil or soy bean oil.

9. The composition of claim 1, wherein said composition comprises about 5% to about 20% by weight of sodium trideceth sulfate.

10. The composition of claim 1, wherein said composition comprises about 1% to about 3% by weight of at least one material comprising lauroamphoacetate or cocoamidopropyl betaine.

11. The composition of claim 1, wherein said composition comprises about 0.1% to about 5% by weight of cocomonoethanolamide.

12. The composition of claim 6, wherein said composition comprises a total salt content of 3% by weight.

* * * * *